United States Patent
Van Dusschoten et al.

(10) Patent No.: US 12,353,000 B2
(45) Date of Patent: * Jul. 8, 2025

(54) OPTICAL FIBER SENSOR FOR SHAPE SENSING, OPTICAL SHAPE SENSING DEVICE, SYSTEM AND METHOD

(71) Applicant: KONINKLIJKE PHILIPS N.V., Eindhoven (NL)

(72) Inventors: Anna Hendrika Van Dusschoten, Eindhoven (NL); Gert Wim 'T Hooft, Eindhoven (NL); Jeroen Jan Lambertus Horikx, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/731,581

(22) Filed: Jun. 3, 2024

(65) Prior Publication Data

US 2024/0319435 A1   Sep. 26, 2024

Related U.S. Application Data

(63) Continuation of application No. 17/274,849, filed as application No. PCT/EP2019/075094 on Sep. 19, 2019, now Pat. No. 12,001,049.

(30) Foreign Application Priority Data

Sep. 20, 2018   (EP) ..................................... 18195654

(51) Int. Cl.
    *G02B 6/02* (2006.01)
    *A61B 5/00* (2006.01)
    (Continued)

(52) U.S. Cl.
    CPC .......... *G02B 6/02042* (2013.01); *A61B 5/065* (2013.01); *A61B 5/6852* (2013.01);
    (Continued)

(58) Field of Classification Search
    None
    See application file for complete search history.

(56) References Cited

U.S. PATENT DOCUMENTS 8,773,650 B2   7/2014   Froggatt
9,784,569 B2   10/2017  Froggatt
(Continued)

FOREIGN PATENT DOCUMENTS

WO   2013136247   9/2013
WO   2015/017270   2/2015
(Continued)

OTHER PUBLICATIONS

International Search Report and Written Opinion Dated Dec. 6, 2019 For International Application No. PCT/EP2019/075094 Filed Sep. 19, 2019.

*Primary Examiner* — Jerry Rahll

(57) ABSTRACT

The present invention relates to an optical fiber sensor for shape sensing, comprising an optical fiber having embedded therein a number of at least four fiber cores (1 to 6) arranged at a distance from a longitudinal center axis (0) of the optical fiber, the number of fiber cores (1 to 6) including a first subset of at least two fiber cores (1, 3, 5) and a second subset of at least two fiber cores (2, 4, 6), the fiber cores (2, 4, 6) of the second subset being arranged to provide a redundancy in a shape sensing measurement of the fiber sensor (12'). The fiber cores (1, 3, 5) of the first subset are distributed in azimuthal direction around the center axis (0) with respect to one another, and each fiber core (2) of the second subset is arranged in non-equidistantly fashion in azimuthal direction
(Continued)

around the center axis (0) with respect to two neighboring fiber cores (1, 3) of the first subset.

17 Claims, 6 Drawing Sheets

(51) Int. Cl.
*A61B 5/06* (2006.01)
*G01B 11/16* (2006.01)
*G02B 6/12* (2006.01)

(52) U.S. Cl.
CPC ............ *G02B 6/022* (2013.01); *A61B 5/6851* (2013.01); *G01B 11/161* (2013.01); *G01B 11/18* (2013.01); *G02B 2006/12138* (2013.01)

(56) References Cited

U.S. PATENT DOCUMENTS

| | | | | |
|---|---|---|---|---|
| 10,094,972 | B2* | 10/2018 | Sasaki | G02B 6/02 |
| 11,199,668 | B1* | 12/2021 | Schlepple | G02B 6/02042 |
| 12,001,049 | B2* | 6/2024 | Van Dusschoten | A61B 5/6852 |
| 2006/0013523 | A1* | 1/2006 | Childlers | G02B 6/02042 385/12 |
| 2006/0024008 | A1 | 2/2006 | Galvanauskas | |
| 2007/0297712 | A1 | 12/2007 | Meneghini | |
| 2011/0109898 | A1* | 5/2011 | Froggatt | G01B 11/168 356/73.1 |
| 2011/0182557 | A1* | 7/2011 | Hayashi | G02B 6/02042 385/127 |
| 2011/0317148 | A1 | 12/2011 | Froggatt | |
| 2013/0108206 | A1* | 5/2013 | Sasaoka | G02B 6/02042 385/11 |
| 2013/0301998 | A1* | 11/2013 | Hayashi | G02B 6/4413 385/100 |
| 2015/0147025 | A1 | 5/2015 | Westbrook | |
| 2016/0238783 | A1 | 8/2016 | Nagashima | |
| 2016/0047976 | A1 | 12/2016 | Schade | |
| 2017/0123146 | A1 | 5/2017 | Chen | |
| 2017/0235042 | A1 | 8/2017 | Sasaki | |
| 2018/0266812 | A1* | 9/2018 | Sasaki | A61B 1/00165 |
| 2019/0234727 | A1* | 8/2019 | Roye | B25J 18/00 |
| 2022/0049950 | A1* | 2/2022 | Van Dusschoten | A61B 5/065 |

FOREIGN PATENT DOCUMENTS

| | | |
|---|---|---|
| WO | 2015193191 | 12/2015 |
| WO | 2016/099976 | 6/2016 |
| WO | 2016/122742 | 8/2016 |
| WO | 2018/009342 | 1/2018 |
| WO | 2018/075911 | 4/2018 |

* cited by examiner

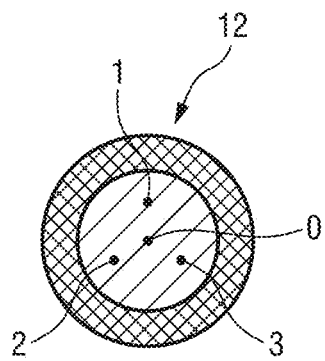
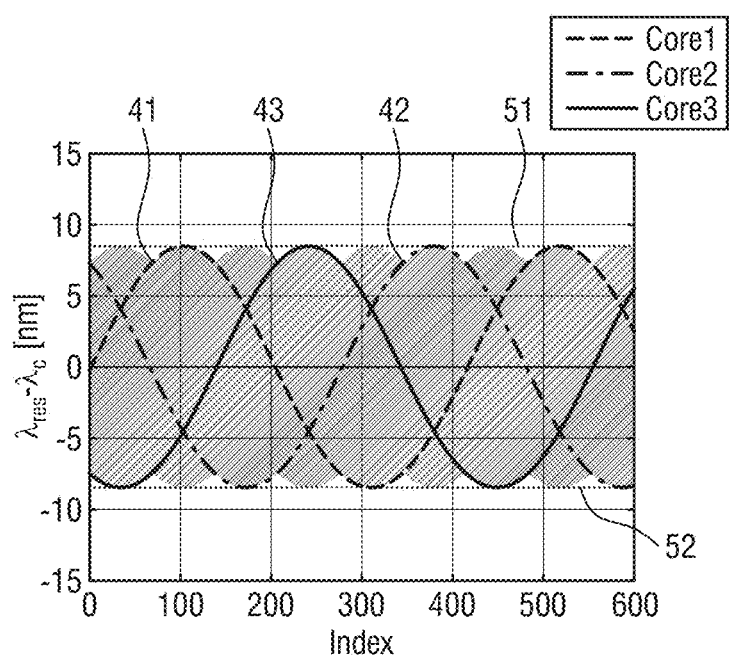
FIG.3A    FIG.3B
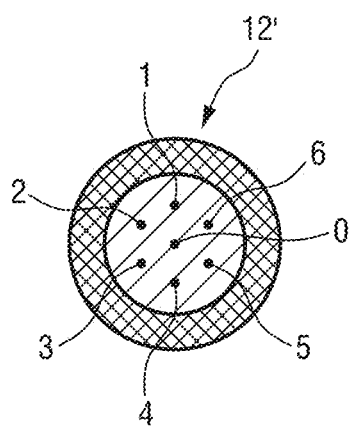
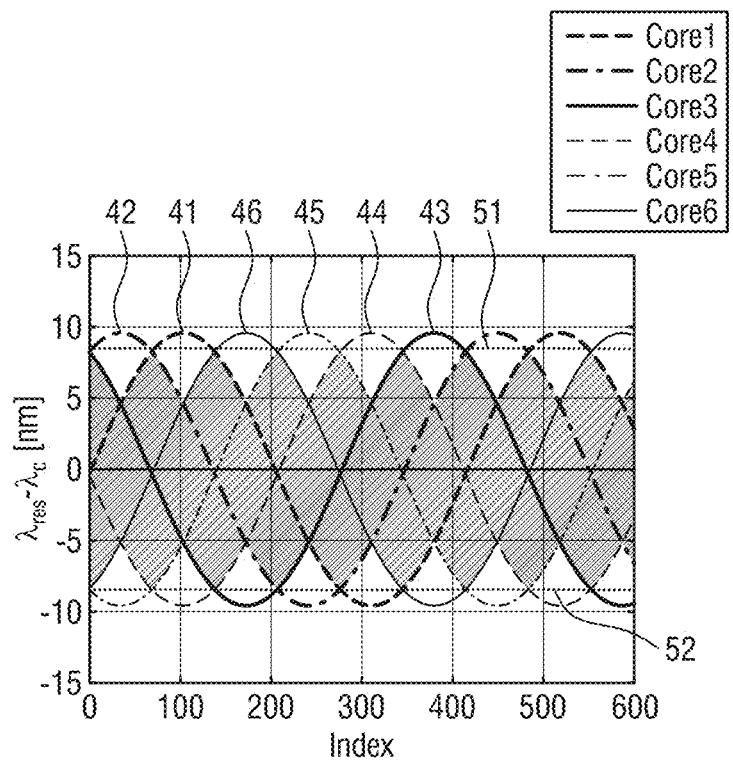
FIG.4A    FIG.4B

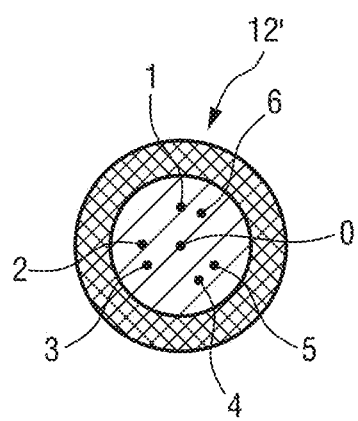
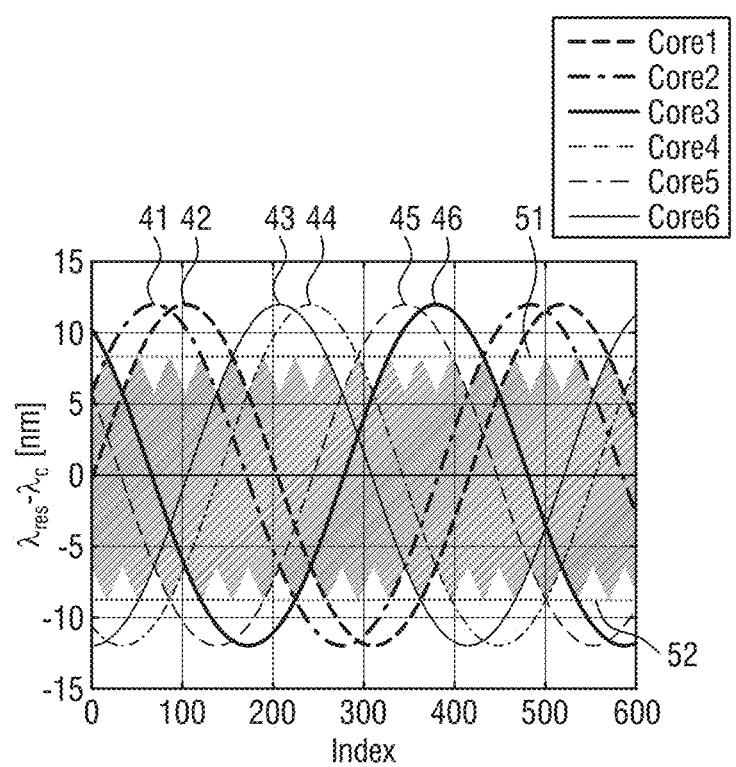
FIG.5A  FIG.5B
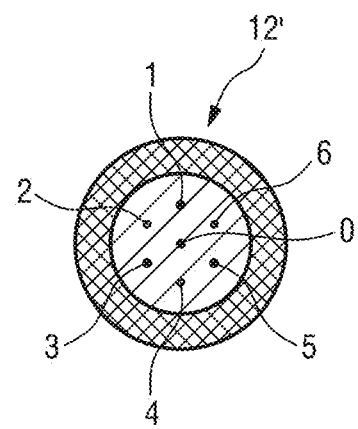
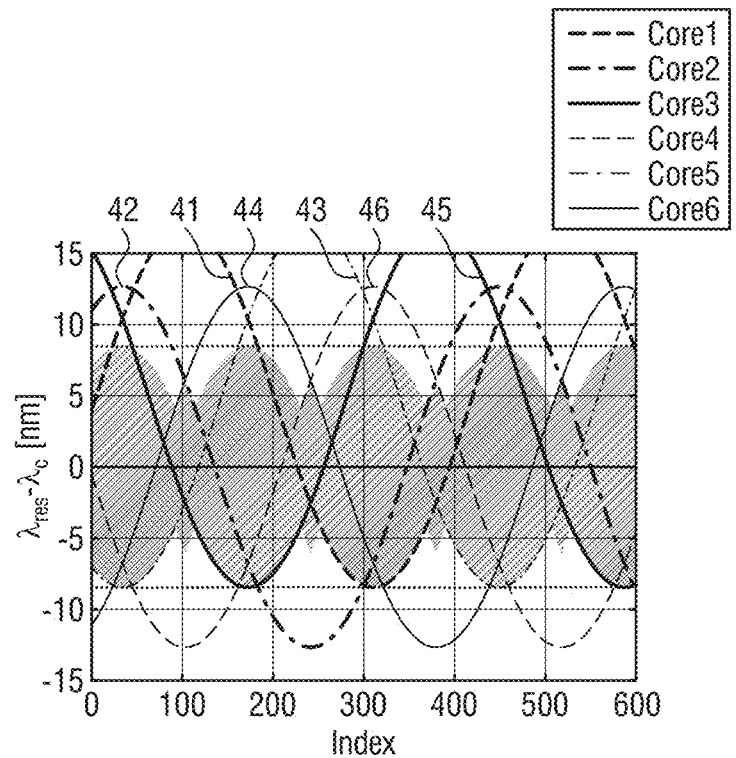
FIG.6A  FIG.6B

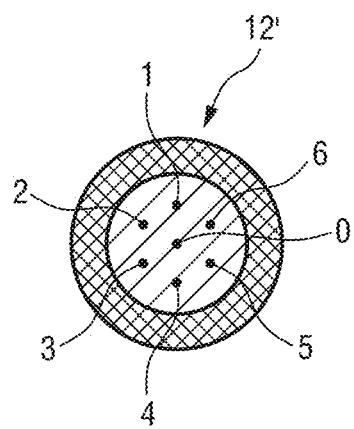
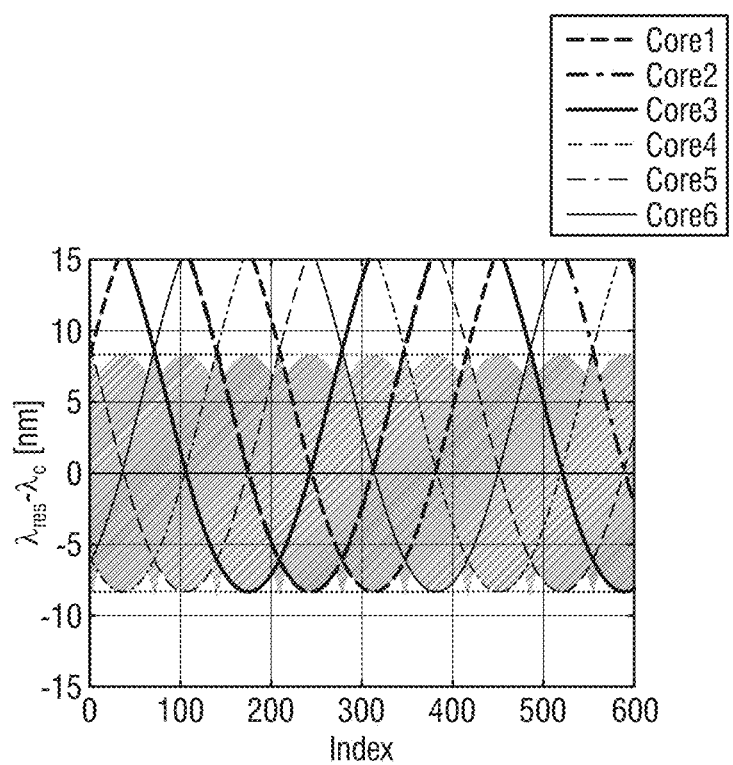
FIG.7A  FIG.7B
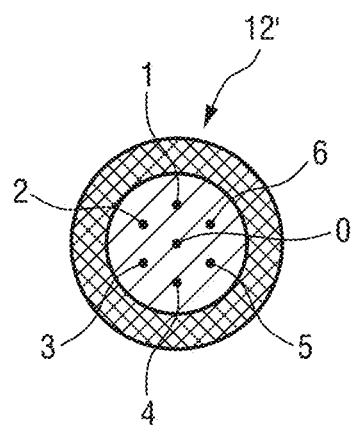
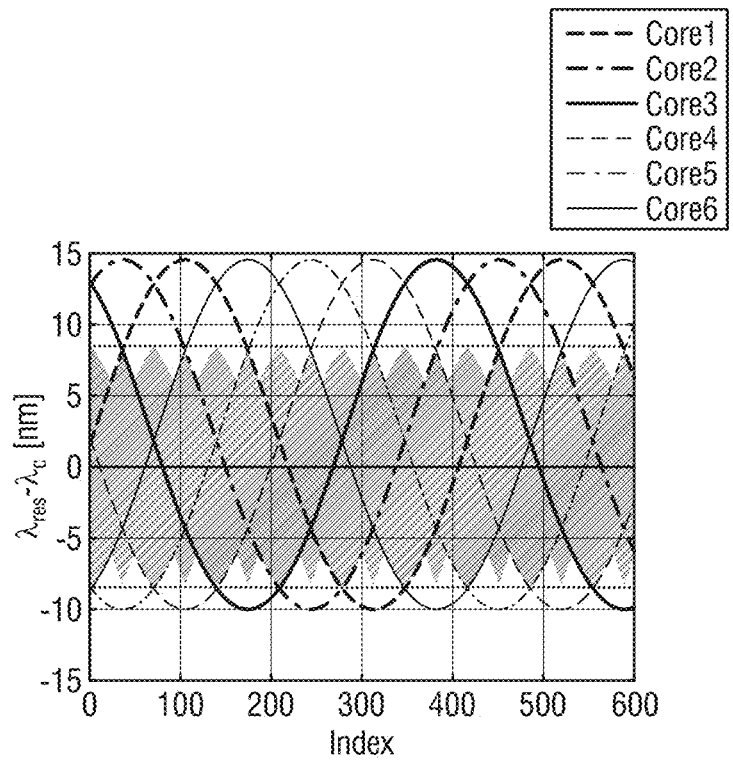
FIG.8A  FIG.8B

OPTICAL FIBER SENSOR FOR SHAPE SENSING, OPTICAL SHAPE SENSING DEVICE, SYSTEM AND METHOD

CROSS REFERENCE TO RELATED APPLICATIONS

This application is a Continuation of U.S. patent application Ser. No. 17/274,849 filed Mar. 10, 2021, which is the U.S. National Phase application under 35 U.S.C. § 371 of International Application No. PCT/EP2019/075094 filed Sep. 19, 2019, which claims the benefit of European Patent Application Number 18195654.1 filed Sep. 20, 2018. These applications are hereby incorporated by reference herein.

FIELD OF THE INVENTION

The present invention generally relates to the field of optical shape sensing. In particular, the present invention relates to an optical fiber sensor for use in optical shape sensing comprising a number of fiber cores arranged in a radial distance from a center axis of the fiber. The present invention further relates to an optical shape sensing device comprising such an optical fiber sensor, and an optical shape sensing system, comprising such an optical fiber sensor. Furthermore, the invention relates to an optical shape sensing method using the optical fiber sensor.

BACKGROUND OF THE INVENTION

Optical shape sensing (OSS) is a technology with which the three-dimensional shape of a special optical fiber can be reconstructed from the reflections of light within the fiber. This technology enables, for example, real-time 3D visualization of the full shape of devices like medical devices, for example catheters and guidewires. The shapes of the medical devices can be overlaid on X-ray images or a pre-operative CT scan. In this way, a physician can navigate the devices during a procedure without the need of X-ray tracking.

In optical shape sensing, an optical fiber sensor, also referred to as optical shape sensing fiber, is interrogated with light coupled into the fiber cores of the fiber, and distributed strain and temperature signals are obtained from backscattered spectra obtained with an interrogator unit incorporating interferometers. A standard optical fiber sensor has three outer fiber cores (in the present description, fiber cores arranged spaced apart from the center axis of the fiber are also denoted as outer fiber cores) helically wound around a fourth core, which is arranged in the radial center of the fiber. The responses of the fiber cores to strain and temperature are measured as phase differences of the optical signals from the interferometers, as a function of delay position along the fiber sensor. The phase differences are obtained with respect to a reference measurement in which the fiber sensor is in a well-defined shape, for example a completely straight shape. From the phase differences of the fiber cores, the strain and temperature differences can be deduced for each fiber core. The strain signals will be the sum of bend strain in two orthogonal directions, as well as twist strain and axial strain, the latter being the strain in the longitudinal direction of the optical fiber sensor. From these four position dependent quantities, the shape of the fiber sensor can be reconstructed. For high-accuracy shape sensing, accurate fiber sensor properties are needed in the shape reconstruction model. These properties can be determined for each individual optical fiber in a calibration process.

A further extension of the shape sensing technology is to be able to distinguish the effect of temperature from the effect of axial strain. In order to do so at least one additional core with a different temperature sensitivity is needed, as, for example, described in WO 2016/099976 A1.

As described above, the shape of the optical sensing fiber is calculated from the position dependent strain signals measured for several, typically four cores inside the fiber. For example, bending the fiber in the plane defined by a fiber core and the fiber center will result in a strain on that fiber core if that core is not arranged in the center of the fiber. In this case, the strain $\varepsilon$ is the quotient of the distance $\alpha$ of that core from the center axis of the fiber and the radius r of the bend of that core. The bend strain is measured here relative to the straight and unstrained state of the fiber. The magnitude of the strain can be deduced from the amount of spectral shift of the reflected light. In the case that the fiber cores contain Fiber Bragg Gratings (FBGs), due to the periodic nature of the Bragg gratings, the sensor will reflect the light of one particular wavelength, called the resonance wavelength. In case the fiber core is elongated (positively strained) relative to the reference measurement, the periodicity of the FBGs will increase, resulting in an increase in resonance wavelength. On the other hand, in case of compressive (negative) strain, the periodicity of the FBGs will decrease, resulting in a decrease in resonance wavelength. The lower the radius of curvature of the bend, the larger the shift $\delta\lambda$ in resonance wavelength (in either positive or negative direction, depending on the location of the fiber core in the bend):

$$\delta\lambda = \lambda_o \xi \varepsilon = \frac{\lambda_o \xi \alpha}{r} \sin(\vartheta_{twist}(z) + \varphi) \qquad (1)$$

wherein $\lambda_0$ is the resonance wavelength of the fiber cores, more precisely the FBGs, in the unstrained state, and $\xi$ is a strain-optic number ($\approx 0.8$) that accounts for the strain-induced change of refractive index, which affects the relation between Bragg period and wavelength. The sine function describes the varying location of the outer core as it is helically twisted around the fiber center. $\vartheta_{twist}$ is the cumulative twist angle of the core, which is the sum of the intrinsically present twist in the spun fiber and the externally applied twist. $\varphi$ is an offset angle which is related to the orientation of the bend plane and the angle of the fiber core at a reference position. For reasons of clarity, in equation (1) only strain due to bend is assumed.

When an optical fiber sensor is inserted, for example, in a lumen of a medical device, it will experience a varying radius of curvature. The medical device may be pre-shaped and during handling of the device it will change its form. The smallest radius of curvature encountered by the optical fiber sensor depends on the design of the device, the optical fiber itself and the environment that it is being used in. For example, the vasculature of a human can, for example, be very tortuous. To be able to access these kind of vessels, more flexible devices will be used. An optical fiber sensor inside such medical devices should be able to withstand small radii of curvature. However, there is a limit, which is related to the minimum measurable bend radius of the optical fiber sensor.

In shape sensing, typically a spectrum is recorded for each fiber core by scanning a light source over a fixed wavelength range $\Delta\lambda$ centered on the resonance wavelength of the FBGs in the unstrained situation. The minimum bend radius that has a resonance still inside the measured spectrum is:

$$r_{min} = \frac{2\lambda_0 \xi a}{\Delta\lambda} \quad (2)$$

For a scan range of $\Delta\lambda=17$ nm centered around $\lambda_0=1545$ nm, $\xi=0.8$, and $\alpha=35$ μm, the minimum measurable bend radius will be 5.1 mm. If the optical fiber sensor is bent to lower curvatures, no signal will be measured for a fiber core that is in the bend plane.

It appears from equation (2) that the minimum measurable bend radius can be reduced by reducing the fiber core distance $\alpha$ and/or by increasing the scan wavelength range $\Delta\lambda$. Reducing the outer fiber core distance $\alpha$ has the disadvantage that it reduces the sensitivity to bend strain and also the sensitivity to twist strain, as the sensitivity to twist strain scales with $\alpha^2$. The required accuracy on the twist is high, therefore reducing the outer fiber core distance from the center axis of the fiber is not favorable. Increasing the scan range $\Delta\lambda$ is disadvantageous for other reasons. It decreases the signal to noise ratio, because the resonance peak fills the spectrum relative less. Further, the delay length between two consecutive nodes (data points as a function of position on the fiber) is decreased, giving an increase of data points for the same physical length of the fiber.

WO 2018/075911 A1 proposes to provide an optical fiber sensor with more than three outer fiber cores, wherein the fiber cores are arranged at multiple different radial distances from the center axis of the fiber. For small bend radii to be measured one has to switch to the fiber cores at lower distance which can lead to lower accuracy of the shape sensing measurement. Such a design of an optical fiber sensor thus suffers from a loss of accuracy.

US 2007/0297712 A1 discloses an optical fiber sensor for detecting curvature of a body, the sensor comprising a cladding having an outer periphery. The centralcore has Bragg gratings and is positioned in neutral planes of the cladding. Peripheral cores receive and transmit light.

US 2016/0047976 A1 discloses a fibre-optic sensor that comprises an optical waveguide having at least one first core and a cladding surround the first core, wherein the first core extends substantially over the entire length of the optical waveguide.

US 2006/0024008 A1 discloses a composite waveguide comprising a central core and at least one side core helically wound about the central core and in optical proximity to the central core.

US 2016/0238783 A1 discloses an optical fiber comprising a core group composed of a plurality of cores extending along a fiber axis, a common cladding including the core group and a coating covering an outer periphery of the common cladding.

US 2017/0123146 A1 discloses multicore optical fibers that have randomly arranged cores within a cladding matrix.

WO 2018/009342 A1 discloses a fiber that includes M primary cores and N redundant cores, where M an integer is greater than two and N is an integer greater than one. Interferometric circuitry detects interferometric pattern data associated with the M primary cores and the N redundant cores when the optical fiber is placed into a sensing position.

SUMMARY OF THE INVENTION

It is an object of the present invention to provide an optical fiber sensor enabling shape measurements with small bend radii without reducing fiber core distance from the center axis and/or without increasing the scan wavelength range.

It is a further object of the present invention to provide a device comprising an improved optical fiber sensor.

It is a further object of the present invention to provide an optical shape sensing system allowing for improved shapes sensing measurements.

It is a further object of the present invention to provide an optical shape sensing method allowing for improved shapes sensing measurements.

According to a first aspect of the invention, an optical fiber sensor for shape sensing is provided, comprising an optical fiber having embedded therein a number of at least four fiber cores arranged spaced apart from a longitudinal center axis of the optical fiber, the number of fiber cores including a first subset of at least two fiber cores and a second subset of at least two fiber cores, the fiber cores of the second subset being arranged to provide a redundancy in a shape sensing measurement of the fiber sensor, wherein the fiber cores of the first subset are distributed in azimuthal direction around the center axis with respect to one another, and each fiber core of the second subset is arranged in non-equidistantly fashion in azimuthal direction around the center axis with respect to two neighboring fiber cores of the first subset.

Optionally, a fiber core of the second subset which is arranged between two neighboring fiber cores of the first subset has an angular position which is closer to one of the two neighboring fiber cores of the first subset than to the other of the two neighboring fiber cores of the first subset, wherein the fiber cores of the first subset are arranged equidistantly in azimuthal direction around the center axis with respect to one another, and the fiber cores of the second subset are arranged equidistantly in azimuthal direction around the center axis with respect to one another.

The optical fiber sensor according to the present invention allows for measuring smaller bend radii by providing a redundancy in the number of fiber cores over the standard fiber sensor having three outer cores only. The invention is based on the insight that it is not necessary to provide outer fiber cores in different distances from the center axis in order to reduce the minimum measurable bend radius with the fiber sensor. In the optical fiber sensor according to the present invention, the outer fiber cores of the first subset and the at least one fiber core of the second subset may be arranged at a same radial distance from the center axis of the fiber, wherein this is preferred, but not imperative. In the fiber sensor according to the invention, at least one, preferably each fiber core of the second subset is arranged in non-equidistantly fashion in azimuthal direction around the center axis with respect to two neighboring fiber cores of the first subset. This means, an outer fiber core of the second subset which is arranged between two neighboring outer fiber cores of the first subset has an angular position which is closer to one of the neighboring outer fiber cores of the first subset than to the other of the two neighboring outer fiber cores of the first subset. This leads to a certain asymmetry between the outer fiber cores of the first subset and the fiber cores of the second subset in terms of angular position around the center axis. As will be described in more detail in the present description, such an arrangement of outer fiber cores is suitable to reduce the minimum measurable bend radius without increasing the scan wavelength range and/or reducing the fiber core distance from the center axis.

While an asymmetry may exist between the angular arrangement of the fiber cores of the second subset and the fiber cores of the first subset, the overall arrangement of all fiber cores may be symmetrical. For example, one can consider one outer fiber core of the first subset and one neighboring outer fiber core of the second subset as forming a pair of outer fiber cores, and the pairs present in the fiber may form a symmetrical arrangement of fiber core pairs, if the difference in angular position of the fiber cores in each pair is the same and the pairs have equal differences in angular position around the center axis with respect to one another. It is, however, also possible to vary the difference in angular position between the two fiber cores in the pairs and/or to vary the difference of angular position between the pairs so that there is no symmetry in the overall arrangement of the fiber cores of the first and second subsets.

An example of an overall symmetrical arrangement may be an arrangement in which the first and second subsets each include three outer fiber cores, and the outer fiber cores of the first subset may be placed at 0°, 120°, 240°, and the outer fiber cores of the second subset may be placed at 30°, 150°, 270° around the center axis.

An angle between the angular position of one fiber core of the second subset in azimuthal direction around the center axis and the angular position of one of two neighboring fiber cores of the first subset may be at least 10%, or at least 20%, or at least 40% less than a half angle between the angular positions of the two neighboring fiber cores of the first subset. In an embodiment of the fiber sensor with three outer cores in the first subset and three outer cores in the second subset, the angle may be in a range from 20° to 40°, e.g. about 30°.

The fiber cores of the first and second subsets of fiber cores may be helically wound around the center axis of the fiber sensor. A central fiber core may be arranged to the center axis and extending along same.

The fiber cores of the first subset and the fiber cores of the second subset may have one or more fiber Bragg gratings along the length of the respective fiber core.

The second subset of fiber cores may include three or more fiber cores.

In another embodiment, which may be combined with any one of the embodiments described before, an optical property of the fiber cores of the second subset differs from the optical properties of the fiber cores of the first subset.

An optical property in this regard may be the resonance wavelength of the fiber cores in an unstrained state thereof. In an embodiment, a first resonance wavelength of the fiber cores of the first subset in response to light introduced into the fiber cores in an unstrained state thereof and a second resonance wavelength of the at least one fiber core of the second subset in an unstrained state thereof may differ from one another. This measure is also suitable to reduce the minimum measurable bend radius of the optical fiber.

A further measure to reduce the minimum measurable bend radius of the optical fiber which may also be combined with any of the embodiments above is to decenter the first resonance wavelength of the fiber cores of the first subset and/or the second resonance wavelength of the at least one fiber core of the second subset with respect to a center wavelength of a scan wavelength range of the light used for interrogating the fiber cores. In this embodiment, the first and second resonance wavelengths may be equal with respect to one another or they may be different.

According to a second aspect of the present invention, an optical shape sensing device is provided comprising an optical fiber sensor according to the first aspect and its embodiments.

The optical shape sensing device may be a medical device, in particular a catheter or guidewire.

According to a third aspect of the invention, an optical shape sensing system is provided, comprising an optical fiber sensor according to the first aspect, and an optical interrogation unit configured to interrogate the fiber cores of the first subset of fiber cores and the at least one fiber core of the second subset of fiber cores of the optical fiber sensor with light in a scan wavelength range and to measure reflection spectra received from the fiber cores of the first subset of fiber cores and the at least one fiber core of the second subset of fiber cores of the optical fiber sensor, and
 an evaluation unit configured to reconstruct the shape of the fiber sensor using the reflection spectra.

The optical shape sensing system according to the invention has the same or similar advantages as described with respect to the optical fiber sensor according to the invention. In particular, the scan wavelength range may be the same as for a standard fiber sensor having three outer cores only, and nevertheless smaller bend radii may be measured with this scan wavelength range than in case of a standard fiber sensor.

In an embodiment, the optical interrogation unit may be configured to set the scan wavelength range such that a center wavelength of the scan wavelength range is decentered with respect to a first resonance wavelength of the fiber cores of the first subset, the resonance wavelength being in response to light introduced into the fiber cores in an unstrained state of the fiber cores, and/or the optical interrogation unit is configured to set the scan wavelength range such that a center wavelength of the scan wavelength range is decentered with respect to a second resonance wavelength of the at least one fiber core of the second subset, the second resonance wavelength being in response to light introduced into the at least one fiber core in an unstrained state of the at least one fiber core. In these embodiments, the scan wavelength range is asymmetrical with respect to the resonance wavelengths of the outer fiber cores of the optical fiber, which is also suitable to measure smaller bend radii of the optical fiber sensor than it is possible with conventional systems.

According to a further aspect, an optical shape sensing method is provided, comprising
 providing an optical fiber sensor according to the first aspect,
 interrogating the fiber cores of the first subset of fiber cores and the at least one fiber core of the second subset of fiber cores with light,
 measuring reflection spectra of light returning from the fiber cores of the first subset of fiber cores and the at least one fiber core of the second subset of fiber cores,
 reconstructing the shape of the optical fiber sensor based on the reflection spectra.

The optical shape sensing method according to the invention has the same or similar advantages as described above.

It is to be understood, that all embodiments described above can be combined with one another in order to provide an optical fiber sensor, an optical shape sensing device, an optical shape sensing system, an optical shape sensing method, all allowing for measuring bend radii of the optical fiber sensor as small as possible.

BRIEF DESCRIPTION OF THE DRAWINGS

These and other aspects of the invention will be apparent from and elucidated with reference to the embodiments described hereinafter. In the following drawings

FIG. 3A shows a cross-section of a standard optical fiber sensor;

FIG. 3B shows a diagram of simulation results for the optical fiber sensor in FIG. 3A, wherein the difference in resonance wavelength and center wavelength of a scan wavelength range is plotted as a function of position on the optical fiber sensor having a bend;

FIG. 4A shows an embodiment of an optical fiber sensor, which has six outer cores;

FIG. 4B shows a diagram of simulation results for the optical fiber sensor in FIG. 4A, wherein the difference in resonance wavelength and center wavelength of a scan wavelength range is plotted as a function of position on the optical fiber sensor;

FIG. 5A shows an embodiment of an optical fiber sensor, which has six outer cores;

FIG. 5B shows a diagram of simulation results for the optical fiber sensor in FIG. 5A, wherein the difference in resonance wavelength and center wavelength of a scan wavelength range is plotted as a function of position on the optical fiber sensor;

FIG. 6A shows an embodiment of an optical fiber sensor, having six outer cores similar to FIG. 4A;

FIG. 6B shows a diagram of simulation results for the optical fiber sensor in FIG. 6A, wherein the difference in resonance wavelength and center wavelength of a scan wavelength range is plotted as a function of position on the optical fiber sensor;

FIG. 7A shows an embodiment of an optical fiber sensor, which has six outer cores similar to FIG. 4A;

FIG. 7B shows a diagram of simulation results for the optical fiber sensor in FIG. 7A, wherein the difference in resonance wavelength and center wavelength of a scan wavelength range is plotted as a function of position on the optical fiber sensor;

FIG. 8A shows the optical fiber sensor in FIG. 7A;

FIG. 8B shows a diagram of simulations results for the optical fiber sensor in FIG. 8A, wherein the difference in resonance wavelength and center wavelength of a scan wavelength range is plotted as a function of position on the optical fiber sensor;

DETAILED DESCRIPTION OF THE INVENTION

Figure 1:
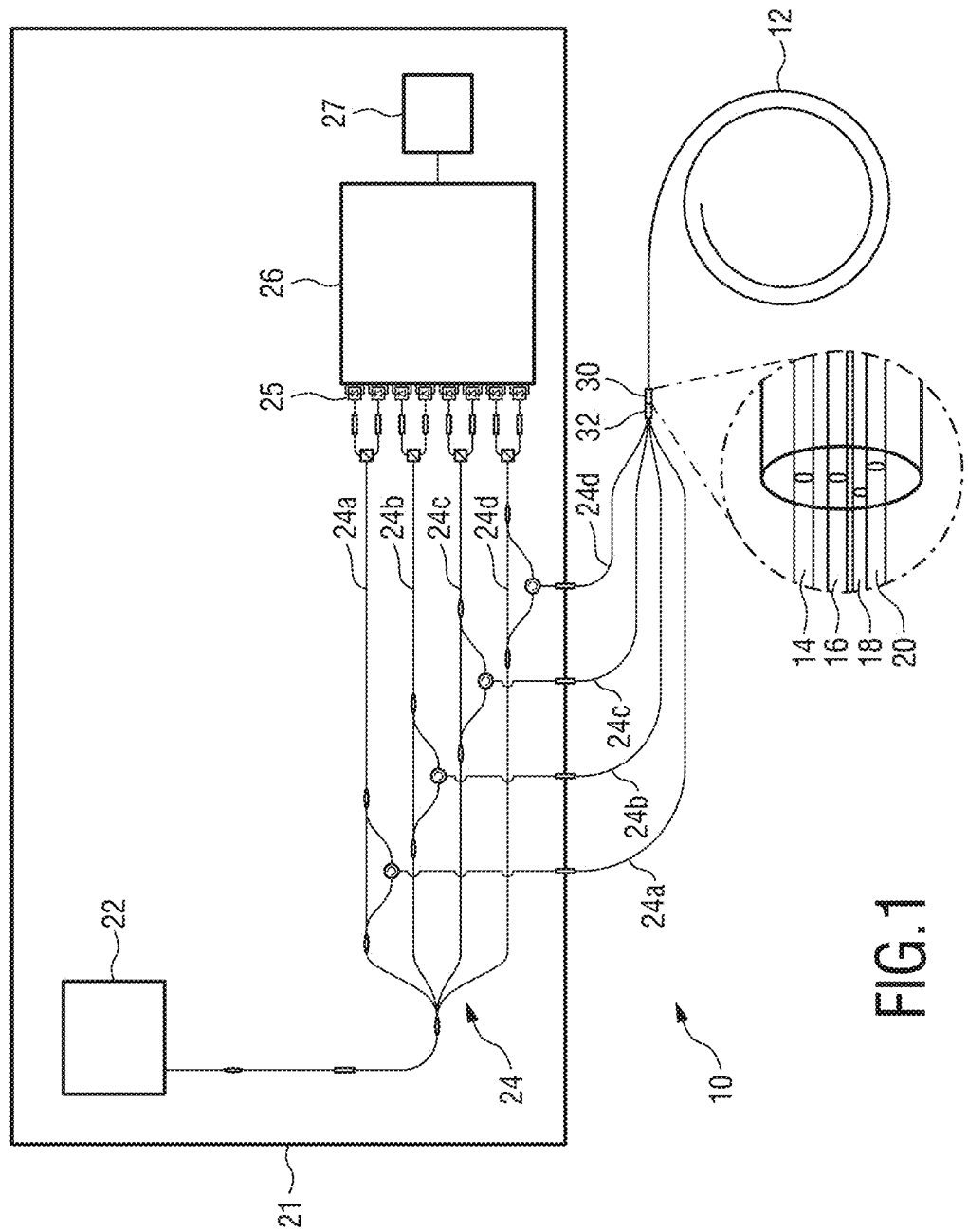
FIG. 1 shows a block diagram illustrating an example of an optical shape sensing system.
Figure 2:
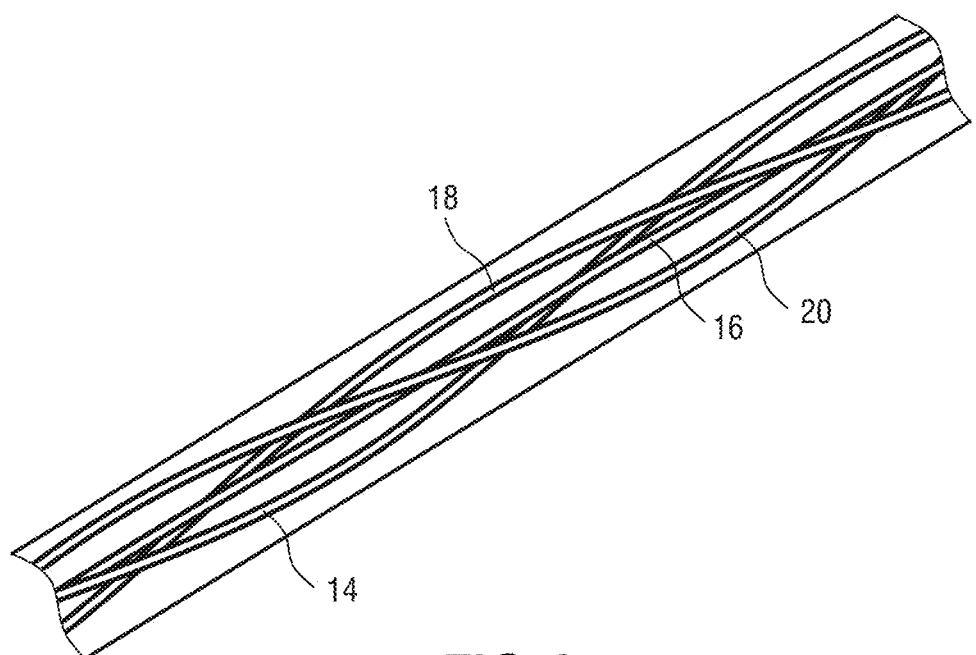
FIG. 2 shows a perspective view of an example of a standard optical fiber sensor.

FIG. 1 schematically shows parts of an optical fiber sensor system 10 configured as a multi-channel optical frequency domain reflectometry (OFDR)-based and distributed-strain sensing system for sensing an optical fiber sensor 12. The optical fiber sensor 12 comprises an optical fiber having embedded therein a plurality of fiber cores 14, 16, 18, 20, in the present example four cores with one center core 16 and three outer cores 14, 18, 20. The optical fiber sensor shown in FIG. 1 is a standard fiber sensor. It is to be noted here that the present invention proposes optical fiber sensor designs having more than three outer cores. FIG. 2 shows a piece of length of the fiber cores 14, 16, 18, 20 with the outer cores 14, 18 20 spiraled around the center core 16. The center core 16 is arranged on the center axis of the optical fiber sensor 12. The outer fiber cores 14, 18, 20 are angularly spaced with respect to one another in azimuthal direction around the longitudinal center axis of the optical fiber sensor 12. The longitudinal center axis coincides with the center core 16. According to a number of four cores in the present example, the angular spacing between neighboring outer cores may be 120°.

With reference again to FIG. 1, the optical shape sensing system 10 comprises an interrogator unit 21. The interrogator unit 21 may comprise a tuneable light source 22 which can be swept through a range of optical frequencies, also referred to as scan wavelength range. The light emitted by the light source 22 is coupled into an optical interferometric network 24 having optical channels 24a, 24b, 24c, 24d according to the number of fiber cores 14, 16, 18, 20 of optical fiber sensor 12. In case the optical fiber sensor 12 has more than four cores, the optical interferometric network 24 may have a corresponding number of optical channels.

When the tuneable light source 22 is swept through a range of optical frequencies, each channel 24a, 24b, 24c, 24d and thus each fiber core 14, 16, 18, 20 of the optical fiber sensor 12 is simultaneously and independently optically interrogated, and the interferometric signals based on the reflection spectrum returning from each of the fiber cores 14, 16, 18, 20 are routed to a processing unit or data acquisition unit 26 via respective photodetectors 25. The distributed strain measurements from the cores 14, 16, 18, 20 using the multiple channel OFDR system may then be exported for further processing to an evaluation unit 27, in particular for three-dimensional shape reconstruction of the optical fiber sensor 12 and for visual display of the reconstructed three-dimensional optical fiber sensor 12.

In embodiments of the optical fiber sensor 12, the fiber cores 14, 16, 18, 20 may have Fiber Bragg Gratings (FBGs) formed by periodic variations in the refractive index. For the sake of simplicity, FBGs having a single resonance wavelength are considered herein. An FBG reflects light of a certain wavelength (resonance wavelength) that depends on the grating period of the FBG, and transmits all other wavelengths. Due to a bend of the optical fiber sensor 12, the grating period is affected by a strain, and measurement of the reflected wavelength for any position along the fiber allows determining the local strain. The optical fiber sensors 12' according to embodiments of the present invention described below, may also comprise such FBGs.

Optical interrogation of the optical fiber sensor 12 gives the information needed to, in principle, reconstruct the three-dimensional shape of the whole fiber sensor in real time. Given an appropriate reference frame, it is possible to know the exact orientation and position of the complete fiber sensor 12 in real time.

When an optical fiber sensor, like the optical fiber sensor 12, is used, for example in a medical device like a catheter or guidewire, the device will change its form during handling of the device. For example, if the device is a catheter for introducing into the vasculature of a human, which can be very tortuous, the device and, thus, the optical fiber sensor 12 will experience bends along its length which may have radii of curvature which can be very small. However, in optical shape sensing technology, there is a limit which is related to the minimum measurable bend radius of the optical fiber sensor.

Referring to equation (2) above, the minimum measurable bend radius of the standard optical fiber sensor 12 will be 5.1 mm for a scan range of $\Delta\lambda=17$ nm centered around the resonance wavelength $\lambda_0=1545$ nm of the fiber cores in an unstrained state, $\xi=0.8$, and a=35 µm (as to the definition of these parameters, see above). If the standard optical fiber sensor 12 is bent to lower curvatures, i.e. to curvatures with a bend radius below 5.1 mm, no signal will be measured for a fiber core that is in the bend plane.

FIG. 3A shows a cross-section of the standard optical fiber sensor 12, wherein the three outer cores are labelled with 1, 2, 3, and the central core is labelled with 0. FIG. 3B shows simulation results (see equation (1)) for the optical fiber sensor 12, with a bend having a radius of 5.1 mm. In FIG. 3B, the difference in $\lambda_{res}$, i.e. the resonance wavelength for each of the fiber cores 1, 2, 3 in the bent state, and $\lambda_c$, i.e. the center wavelength of the scan wavelength range is plotted as function of position on the optical fiber sensor along its length, for the three outer cores 1, 2, 3 separated by 120° in azimuthal direction around the center axis (central core 0). The spectrum of the center core 0 is not depicted in FIG. 3B, as there will be no shift in resonance wavelength due to bend strain for the central core 0. The twist rate of the outer fiber cores 1, 2, 3 is 50 turns per meter and 1 index corresponds to 48.2 µm. The grey-shaded area gives the scan wavelength range needed to cover the shift in resonance wavelength of the outer cores due to the bend. In FIG. 3B, curve 41 shows a simulation result for core 1, curve 42 shows the simulation result for core 2, and curve 43 shows the simulation result for core 3. The minimum scan range needed to always cover the 5.1 mm bend radius (which is, for all orientations of the optical fiber sensor with respect to the bend) is shown in FIG. 3B by dotted lines 51, 52 at $\lambda_{res}-\lambda_c=\pm 8.4$ nm.

FIG. 4A shows an embodiment of an optical fiber sensor 12' according to the invention, which comprises a number of outer fiber cores which is larger than 3. In other words, the optical fiber sensor 12' provides a redundancy by adding further outer fiber cores which provides a redundancy in a shape sensing measurement of the fiber 12' to allow for measuring smaller bend radii of the fiber 12' than with the three outer fiber cores of the standard sensor 12. In FIG. 4A, the outer fiber cores are labelled with reference numerals 1 to 6. The fiber sensor 12' also includes a center core 0, wherein 0 also denotes the center axis of the fiber sensor 12'. So there are three outer fiber cores of a first subset of fiber cores, for example fiber cores 1, 3, 5, and three outer fiber cores of a second subset of fiber cores, for example fiber cores 2, 4, 6 (it is to be noted that the allocation of the fibers to the first subset and the second subset is not critical).

As shown in FIG. 4A, the fiber cores 1, 3, 5 of the first subset and the fiber cores 2, 4, 6 of the second subset have the same radial distance from the center axis (center core 0). Further, the fiber cores 1 to 6 are arranged equidistantly around the center axis in azimuthal direction. The angle between two neighboring fiber cores of the fiber cores 1 to 6 thus is 60°. The fiber cores 1,3,5 may have a first single resonance wavelength in an unstrained state of the fiber 12', and the fiber cores 2,4,6 may have a second single resonance wavelength in an unstrained state of the fiber sensor 12'. In this example, the first and second resonance wavelengths are qual.

The fiber cores of the second subset of fiber cores may be helically wound around the center axis of the sensor 12'.

To be able to distinguish the four position-dependent quantities needed for shape reconstruction with the optical fiber sensor 12', which quantities are bend strain in two orthogonal directions, twist and axial strain, the signals of the central core 0 and at least three of the outer cores 1 to 6 should be known.

FIG. 4B shows the simulation results for the optical fiber sensor 12' in FIG. 4A where again the difference in resonance wavelength $\lambda_{res}$ and center wavelength $\lambda_c$ of the scan wavelength range is plotted as a function of position on the optical fiber sensor 12', as described with respect to FIG. 3B. The grey-shaded area gives the scan wavelength range needed to include the resonances of at least three of the outer cores 1 to 6. In FIG. 4B, curves 41 to 46 show the simulation results for the outer fiber cores 1 to 6 (the result for the center core 0 is again omitted in FIG. 4B). As can be seen from the diagram in FIG. 4B, the black-dotted lines 51 and 52 are not at the maxima of the fiber core signals any more, which means that with the same scan wavelength range (±8.4 nm) a smaller bend radius can be measured. In the present case, a minimum bend radius $r_{min}$ of 4.5 mm can be measured. Comparing the simulation results of FIG. 3B and 4B, it reveals that the redundancy in fiber cores by providing, for example, six outer fiber cores instead of three, the minimum measurable bend radius can be reduced without increasing the scan wavelength range and without decreasing the distance of the outer cores from the center axis.

In order to have a measure for the beneficial effect of redundancy in outer fiber cores in comparison with a standard optical fiber sensor having three outer cores, like optical fiber sensor 12 in FIG. 3A, a gain factor f may be calculated that is obtained by the redundancy due to the amount n of cores without increasing the scan wavelength range:

$$f = \cos\left(\frac{\pi}{n-1} \text{ floor}\left(\frac{n}{2}-2\right)\right), \text{ for } n \geq 4 \qquad (3)$$

where n is the total number of fiber cores (including the center core and n−1 outer fiber cores). For n=4 (standard optical fiber sensor), f is 1. For n=7 (six outer cores and one center core), f is about 0.87. This means that for a symmetrical arrangement of six outer cores (60° angle between two neighboring outer cores), the minimum measurable bend radius can be reduced by a factor of 0.87, i.e. from 5.1 mm to 4.5 mm, with the same scan wavelength range.

The gain factor f and, thus, the minimum measurable band radius, can be further reduced by one or more of the following measures which will be described in connection with further embodiments.

In general, optimization of the gain factor f can be done by changing the fiber core angles with respect to one another, and/or by changing the core optical properties, and/or by introducing an asymmetry between the scan wavelength range and the resonance wavelength of the fiber cores in the unstrained state thereof. These measures will be described hereinafter.

FIG. 5A shows an embodiment of an optical fiber sensor 12' having six outer cores 1 to 6 wherein the difference to the embodiment in FIG. 4A is that the fiber cores 1 to 6 in FIG. 5A are not equidistantly distributed in azimuthal direction around the center core 0 extending along the central axis of the fiber 12'. In the embodiment in FIG. 5A, the angle between some of neighboring fiber cores, for example fiber cores 2 and 3, is smaller than the angle between other neighboring fiber cores, for example fiber cores 1 and 2. For example, the smaller angle between fiber cores 2 and 3, 4 and 5, and 6 and 1 may be 30°, while the larger angle between fiber cores 1 and 2, 3 and 4, and 5 and 6 is 90°. It should be noted that the number of six outer fiber cores as shown in FIG. 5A is exemplary, and any other number of outer fiber cores can be taken as well, as long there is redundancy. In the embodiment in FIG. 5A, a first subset of outer cores 1, 3, 5 are placed at 0°, 120° and 240°, and a second subset of three cores 2, 4, 6 having the same relative angles between them are placed under an angle of θ=30° with respect to the fiber cores 1, 3, 5 of the first subset. For a 7-core optical fiber sensor (six outer fiber cores and one center core) with arbitrary θ, the gain factor f is given by:

$$f = \max\left\{\cos\left(\frac{|\theta| - 2\pi/3}{2}\right), -\sin\left(\frac{|\theta| - 2\pi/3}{2}\right)\right\}, \text{ for } -\frac{\pi}{3} < \theta \leq \pi/3 \quad (4)$$

The lowest gain factor f is obtained for θ=30° (f=0.71) in the 7-core fiber sensor 12'. FIG. 5B shows a diagram similar to FIG. 4B of simulation results for the six outer cores 1 to 6 in FIG. 5A. The grey-shaded area again gives the scan wavelength range needed to include the resonances of at least three outer cores, and the dotted lines 51, 52 depict the minimum scan wavelength range needed to cover the resonances of all fiber cores for the 5.1 mm bend radius.

Thus, with an angle θ=30°, a reduction in minimum measurable bend radius to 3.6 mm can be achieved, which is lower than in the more symmetric case of the embodiment in FIG. 4A with θ=60°, for the same fixed scan wavelength range of ±8.4 nm.

A further measure to optimize the minimum measurable bend radius of an optical fiber sensor is to properly choose the optical properties of the fiber cores in the first and the second subset. Such an optical property which may be varied among the fiber cores may be the resonance wavelength $\lambda_0$ of the fiber cores in an unstrained state thereof. FIG. 6A shows an embodiment of an optical fiber sensor 12', which is geometrically identical with the embodiment in FIG. 4A, comprising a first subset of fiber cores, for example fiber cores 1, 3, 5 and a second subset of fiber cores, for example fiber cores 2, 4, 6. The difference to the embodiment in FIG. 4A is that the resonance wavelengths $\lambda_{0A}$ of the first subset of outer cores in an unstrained state thereof is different from the resonance wavelengths $\lambda_{0B}$ of the fiber cores of the second subset of fiber cores in an unstrained state thereof. The resonance wavelengths of the fiber cores of the first subset may be decentered from the center wavelength $\lambda_c$ of the scan wavelength range, while the resonance wavelengths of the fiber cores of the second subset is kept at the scan wavelength range center $\lambda_c$. As an example, for the first subset of fiber cores, $\lambda_{0A}-\lambda_c$ may be 4.3 nm, while for the second subset of outer fiber cores $\lambda_{0B}=\lambda_c$. It is also conceivable that $\lambda_{0A,0B}-\lambda_c$ deviates from zero for the first subset of three outer fiber cores as well as for the second subset of three outer fiber cores. FIG. 6B shows simulation results for the optical fiber sensor 12' in FIG. 6A, wherein the difference in resonance wavelength $\lambda_{res}$ in the strained state and the center wavelength $\lambda_c$ of the scan wavelength range is plotted as function of position on the sensor for the outer fiber cores 1-6, as explained with respect to FIG. 3B.

It is also conceivable to combine the embodiment in FIG. 6A with the embodiment in FIG. 5A, i.e. to change the angle positions of the outer fiber cores 1 to 6 in a non-equidistant manner as shown in FIG. 5A.

A further option in combination with the redundancy of outer optical fiber cores in order to reduce the minimum measurable bend radius is to introduce an asymmetry between the resonance wavelengths, for example of the FBGs of the unstrained fiber cores, and the center wavelength of the scan wavelength range that is used to interrogate the fiber cores. This means $\lambda_0 \neq \lambda_c$, even in case $\lambda_0$ is the same for all fiber cores. To this end, the interrogation unit 21 of the optical shape sensing system 10 in FIG. 1 is configured to set the center wavelength $\lambda_c$ such that the center wavelength differs from the resonance wavelengths of the fiber cores 1 to 6. FIG. 7A and FIG. 8A show in each case a cross-section of an optical fiber sensor 12' having six outer fiber cores 1 to 6 and one center core 0 in each case. The geometrical designs of the optical sensing fiber 12' in FIG. 7A and in FIG. 8A are the same with respect to one another. In the embodiment of FIG. 7A, the scan wavelength range is set such that the resonance wavelength $\lambda_0$ of the unstrained fiber cores 1 to 6 is completely at the edge of the scan range, i.e. $\lambda_0-\lambda_c$=8.4 nm in this example. In this case, the minimum measurable bend radius becomes as low as 2.6 mm for a 16.7 nm scan range. This configuration however means that the resonances are only in the scan wavelength range in case of the limit of a completely straight fiber. If one defines the minimum radius of curvature for which all fiber cores 1 to 6 are still in the measured spectrum with $r_x$, then $r_x=\infty$ in this case. This may be an undesirable situation, as the redundancy in fiber cores cannot be used for anything else any more, not even in cases of lower curvature. Lowering the decentering $\lambda_0-\lambda_c$ will lower $r_x$ as well. FIG. 8A and FIG. 8B give an example, in which a trade-off is made between $r_{min}$ which is the smallest radius still measurable with four fiber cores (including the center core) and $r_x$. For example, if $\lambda_0-\lambda_c$=2.3 nm for all outer fiber cores 1 to 6, $r_{min}$=3.5 mm and $r_x$=7.0 mm.

In the following table 1, the simulation results of the standard case in FIG. 3A and the embodiments in FIG. 4A, 5A, 6A, 7A and 8A are summarized. In table 1, the gain factor f, $r_{min}$ (the smallest radius of curvature still measurable with four fiber cores including the center core) and $r_x$ (the minimum radius of curvature for which all fiber cores are still in the measured spectrum) are listed.

TABLE 1

| | | | | | |
|---|---|---|---|---|---|
| 16.7 | 4 120° between outer cores | 3A | 1 | 5.1 | 5.1 |
| 16.7 | 7 60° between outer cores | 4A | 0.87 | 4.5 | 5.1 |
| 16.7 | 7 Core angles: 0°, 30°, 120°, 150°, 240°and 270° | 5A | 0.71 | 3.6 | 5.1 |
| 16.7 | 7 $\lambda_0$-$\lambda_c$ is 4.3, 0, 4.3, 0, 4.3 and 0 nm | 6A | 0.66 | 3.4 | 10.6 |
| 16.7 | 7 $\lambda_0$-$\lambda_c$ is 2.8, −2.8, 2.8, −2.8, 2.8 and −2.8 nm | — | 0.75 | 3.9 | 7.8 |
| 16.7 | 7 $\lambda_0$-$\lambda_c$ is 8.4 nm for all cores | 7A | 0.50 | 2.6 | ∞ |
| 16.7 | 7 $\lambda_0$-$\lambda_c$ is 2.3 nm for all cores | 8A | 0.68 | 3.5 | 7.0 |

Table 1 also includes an embodiment in line 5 of table 1, in which $\lambda_0-\lambda_c$ deviates from zero for the outer fiber cores of the first subset as well as for the outer fiber cores of the second subset as mentioned above, wherein $\lambda_0-\lambda_c$=2.8 nm for the outer fiber cores of the first subset and $\lambda_0-\lambda_c$=−2.8 nm for the outer fiber cores of the second subset.

The above described measures of optimizing the design of the optical fiber sensor 12' and optimizing the interrogator unit 21 (FIG. 1) which provides the scan range of interrogation of the fiber cores of the optical fiber sensor 12' can all be combined for an application to be performed.

For example, the resonance wavelength $\lambda_0$ in the unstrained state of the fiber cores may deviate from fiber core to fiber core due to some other design constraint. For example, in case it is desired to distinguish temperature from axial strain, at least one fiber core with a temperature sensitivity different from the other cores has to be used. This can result in a deviating $\lambda_0$ for this fiber core. For the case of a 7-fiber core shape sensing fiber with a design similar to the one in FIG. 6A, some options will be described in the following. To this end, it is defined $\Delta=\lambda_{0,A}-\lambda_{0,B}$, where A and B denote the two subsets of three outer cores separated by 60°. It is now possible to calculate $r_{min}$ and $r_x$ for a certain $\Delta$ and $\lambda_{0,A}-\lambda_c$. The results are given in FIGS. 9A and 9B and in FIG. 10.

Figure 9A:
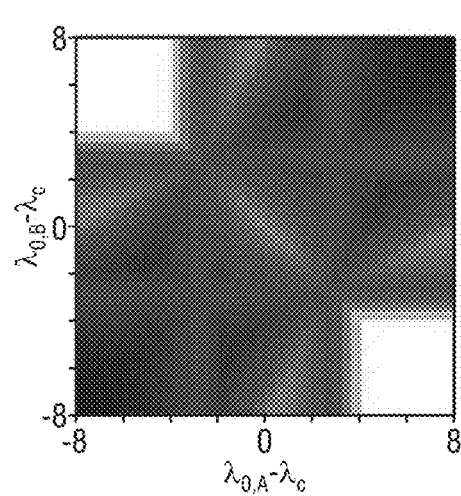
FIG. 9A and 9B show diagrams of simulation results for a gain factor $f=r_{min}/r_0$ and for $r_0/r_x$ as function of a decentering of a center wavelength of a scan wavelength range with respect to resonance wavelengths of two sets of outer cores.
Figure 9B:
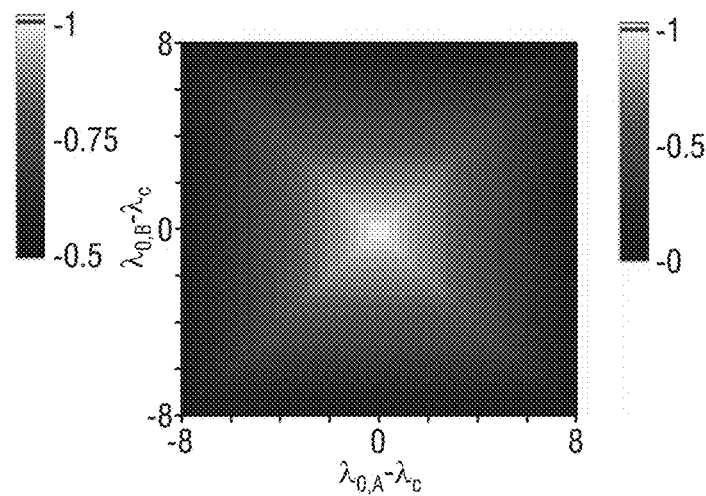
Figure 10:
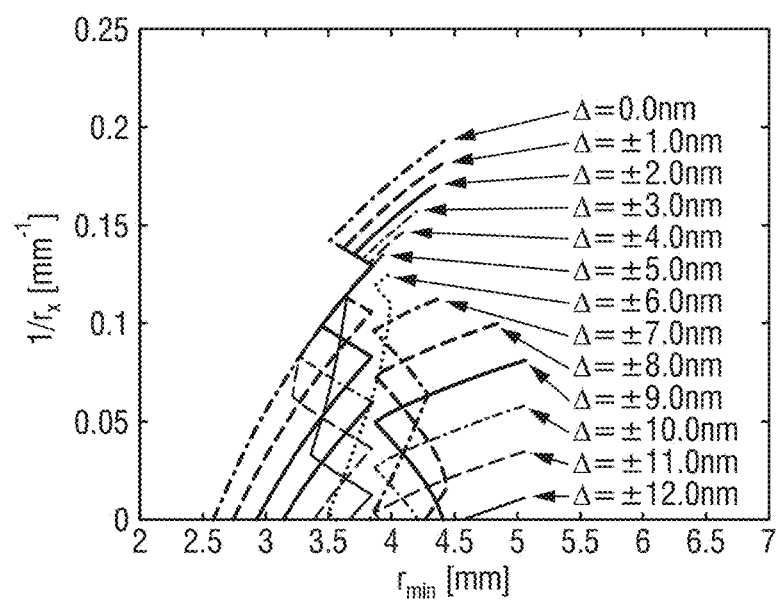
FIG. 10 shows a diagram of simulation results for the smallest radius of curvature measurable with six outer cores as function of the smallest radius still measurable with four cores for various optical fiber sensor designs.

In FIG. 10, $1/r_x$ is plotted as a function of $r_{min}$ for a plurality of $\Delta$ in the range from $\Delta=0.0$ nm up to $\Delta=\pm12.0$ nm. FIG. 9A shows simulation results for the gain factor $f=r_{min}/r_0$, and FIG. 9B for the quantity $r_0/r_x$, each as function of $\lambda_{0,A}-\lambda_C$ and $\lambda_{0,B}-\lambda_C$. $r_0$ is the minimum measurable bend radius for the standard fiber design having three outer cores as shown in FIG. 3A.

The two plots of 9A and 9B are combined in FIG. 10. FIG. 10 shows the highest curvature $(1/r_x)$ measurable with 7 fiber cores as function of the smallest radius $r_{min}$ still measurable with four fiber cores (including the center core) of the fiber sensor 12' for various sensor designs expressed by $\Delta$. $r_{min}$ ranges from 2.6 nm to 5.9 mm and $r_x$ ranges from 5.1 nm to infinity on the edges. It can be taken from FIG. 9A, 9B and 10 that there are "local" optimal designs which maximally leverage the trade-off between $r_{min}$ and $r_x$. For example, the case of $\Delta=0$ nm represents an optimum since all curves with $\Delta\neq0$ nm give rise to larger or at best equal values for $r_{min}$. For the case of $\Delta=0$ nm it is possible to derive an expression for the minimum measurable bend radius as a function of the offset in scan wavelength range. To this end, a relative scan wavelength range offset $O_f$ is introduced with $O_f=|2(\lambda_{0,A}-\lambda_c)/\Delta\lambda|=|2(\lambda_{0,B}-\lambda_c)/\Delta\lambda|$, where $\Delta\lambda$ represents the full scan range, which is 16.7 nm in the present example. The gain factor $f=r_{min}/r_0$ is given by:

$$f = \frac{1}{2}\frac{\sqrt{3}}{1+O_f} \text{ while } 0 \leq O_f \leq \frac{\sqrt{3}-1}{\sqrt{3}+1} \quad (5)$$

$$f = \frac{1}{2}\frac{1}{1-O_f} \text{ while } \frac{\sqrt{3}-1}{\sqrt{3}+1} \leq O_f \leq \frac{1}{3}$$

$$f = \frac{1}{1+O_f} \text{ while } \frac{1}{3} \leq O_f \leq 1$$

$$\frac{r_0}{r_x} = 1 - O_f \text{ while } 0 \leq O_f \leq 1$$

From equation (5) and FIG. 10 it is clear that there is an optimum at $O_f=(\sqrt{3}-1)/(\sqrt{3}+1)$ so that f=0.68 and $r_0/r_x=0.73$. For a scan range of 16.7 nm and $r_0=5.1$ mm this constitutes a design with $r_{min}=3.5$ mm and $r_x=7.0$ mm (which is exactly the example as given in FIG. 8A). For a slightly smaller $r_{min}$, $r_x$ becomes directly much larger. This local optimum is achieved for $\lambda_{0,A}-\lambda_c=2.3$ nm. Similar considerations can be made for other shape sensing fiber designs.

The above-described aspects are all valid in case of redundancy, i.e. the number of fiber cores in the fiber sensor is larger than the number of quantities needed to accurately sense the shape of the optical fiber sensor 12'. However, it can be advantageous to use the same aspects also in cases when even though strictly speaking there is no overall redundancy. It might be acceptable to lose information on less important quantities in order to create temporarily or spatially "redundancy" for essential quantities required for shape sensing. For example, for some measurements or at some particular locations, e.g. with short bends having a smaller radius of curvature, only the signals of some of the fiber cores might be used so that that smaller bend radius still can be probed. This might compromise accuracy a little, or this could be compensated with (temporal or spatial) interpolation or extrapolation of signals. This will be explained in more detail below.

With again reference to FIG. 6A, showing an optical fiber sensor 12' with 7-cores in total, wherein three temperature sensitive fiber cores have different resonance wavelengths $\lambda_0$ in an unstrained state therefore, axial strain, temperature, bend strain in two orthogonal directions and twist strain can be measured, because the number of quantities to be measured (five) is smaller than the number of fiber cores (seven). The smallest radius of curvature for which the afore-mentioned quantities can be measured is 10.6 mm ($r_x$). Below this radius and above $r_{min}=3.2$ mm, only three outer fiber cores are still in the spectrum. With these three outer fiber cores and the center fiber core, still bend strain in two orthogonal directions and twist strain can be measured, as well as the sum of the effects of axial strain and temperature. Because axial strain and temperature cannot be separated anymore, the accuracy of the other signals is compromised, but for a small distance the remaining accuracy may still be sufficient. There may be many applications where the probability of tight bends being present in the optical fiber sensor 12' is low and, if they occur, the length of the tight bend is short and might even be at the end of the shape, for example in medical devices, reducing the effect on total shape accuracy even more. As said before, the temperature and axial strain separation at the places where 7 fiber cores are still available may be inter- or extrapolated to compensate for the loss in accuracy. Or, in other situations, the temperature and axial strain separation for a measurement with $r_{min}<r<r_x$ may be inter- or extrapolated from measurements that are close in time to the measurement with $r>r_x$.

The above aspects which are suitable to reduce the minimum measurable bend radius using one or more of the embodiments of the optical fiber sensor 12' described above can be used in an optical shape sensing method. In the method, the optical fiber sensor (12') is provided. The fiber cores (1, 3, 5) of the first subset of fiber cores and the fiber cores (2, 4, 6) of the second subset of fiber cores are interrogated with light. Reflection spectra of light returning from the fiber cores (1, 3, 5) of the first subset of fiber cores and the at least one fiber core (2, 4, 6) of the second subset of fiber cores are measured, and the shape of the optical fiber sensor (12') based on the reflection spectra is reconstructed. The method can be performed with the system 10 in FIG. 1, wherein, as mentioned above, the system 10 has a corresponding number of optical channels 24a-24d which is larger than four. The fiber sensors 12' described above may be comprised by a medical device, like a catheter or guidewire.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An optical fiber sensor for shape sensing, comprising: an optical fiber having embedded therein a number of at least four fiber cores arranged spaced apart from a longitudinal center axis of the optical fiber, the number of fiber cores including a first subset of at least two fiber cores and a second subset of at least two fiber cores, the fiber cores of the second subset being arranged to provide a redundancy in a shape sensing measurement of the fiber sensor, wherein the fiber cores of the first subset are distributed in azimuthal direction around the center axis with respect to one another, and each fiber core of the second subset is arranged in non-equidistantly fashion in azimuthal direction around the center axis with respect to two neighboring fiber cores of the first subset, wherein a fiber core of the second subset which is arranged between two neighboring fiber cores of the first subset has an angular position which is closer to one of the two neighboring fiber cores of the first subset than to the other of the two neighboring fiber cores of the first subset, wherein an optical property of the fiber cores of the second subset differs from the optical properties of the fiber cores of the first subset.

2. The optical fiber sensor of claim 1, wherein the fiber cores of the first subset are arranged equidistantly in azimuthal direction around the center axis with respect to one another, and the fiber cores of the second subset are arranged equidistantly in azimuthal direction around the center axis with respect to one another.

3. An optical fiber sensor for shape sensing, comprising: an optical fiber having embedded therein a number of at least four fiber cores arranged spaced apart from a longitudinal center axis of the optical fiber, the number of fiber cores including a first subset of at least two fiber cores and a second subset of at least two fiber cores, the fiber cores of the second subset being arranged to provide a redundancy in a shape sensing measurement of the fiber sensor, wherein the fiber cores of the first subset are distributed in azimuthal direction around the center axis with respect to one another, and each fiber core of the second subset is arranged in non-equidistantly fashion in azimuthal direction around the center axis with respect to two neighboring fiber cores of the first subset, wherein a fiber core of the second subset which is arranged between two neighboring fiber cores of the first subset has an angular position which is closer to one of the two neighboring fiber cores of the first subset than to the other of the two neighboring fiber cores of the first subset, wherein the fiber cores of the first subset have a first resonance wavelength in response to light introduced into the fiber cores in an unstrained state thereof, and the fiber cores of the second subset have a second resonance wavelength in response to light introduced into the fiber cores in an unstrained state thereof, the second resonance wavelength being different from the first resonance wavelength.

4. An optical fiber sensor for shape sensing, comprising: an optical fiber having embedded therein a number of at least four fiber cores arranged spaced apart from a longitudinal center axis of the optical fiber, the number of fiber cores including a first subset of at least two fiber cores and a second subset of at least two fiber cores, the fiber cores of the second subset being arranged to provide a redundancy in a shape sensing measurement of the fiber sensor, wherein the fiber cores of the first subset are distributed in azimuthal direction around the center axis with respect to one another, and each fiber core of the second subset is arranged in non-equidistantly fashion in azimuthal direction around the center axis with respect to two neighboring fiber cores of the first subset, wherein a fiber core of the second subset which is arranged between two neighboring fiber cores of the first subset has an angular position which is closer to one of the two neighboring fiber cores of the first subset than to the other of the two neighboring fiber cores of the first subset, wherein the fiber cores of the first subset are arranged equidistantly in azimuthal direction around the center axis with respect to one another, and the fiber cores of the second subset are arranged equidistantly in azimuthal direction around the center axis with respect to one another.

5. The optical fiber sensor of claim 4, wherein an angle between the angular position of one fiber core of the second subset in azimuthal direction around the center axis and the angular position of one of two neighboring fiber cores of the first subset is at least 10% less than a half angle between the angular positions of the two neighboring fiber cores of the first subset.

6. The optical fiber sensor of claim 4, wherein the first subset of fiber cores includes three fiber cores arranged at a radial distance from the longitudinal center axis, and the second subset of fiber cores includes three fiber cores arranged at a radial distance from the longitudinal center axis.

7. The optical fiber sensor of claim 6, wherein an angle between the angular position of one fiber core of the second subset in azimuthal direction around the center axis and the angular position of one of two neighboring fiber cores of the first subset is in a range from 20° to 40°.

8. The optical fiber sensor of claim 6, wherein an angle between the angular position of one fiber core of the second subset in azimuthal direction around the center axis and the angular position of one of two neighboring fiber cores of the first subset is about 30°.

9. The optical fiber sensor of claim 4, wherein an optical property of the fiber cores of the second subset differs from the optical properties of the fiber cores of the first subset.

10. The optical fiber sensor of claim 4, wherein the fiber cores of the first subset have a first resonance wavelength in response to light introduced into the fiber cores in an unstrained state thereof, and the fiber cores of the second subset have a second resonance wavelength in response to light introduced into the fiber cores in an unstrained state thereof, the second resonance wavelength being different from the first resonance wavelength.

11. The optical fiber sensor of claim 4, wherein the fiber cores of the first subset of fiber cores and the fiber cores of the second subset of fiber cores have an equal distance from the center axis.

12. The optical fiber sensor of claim 4, wherein the optical fiber core further comprises a central fiber core arranged on the center axis of the fiber.

13. The optical shape sensing device, comprising an optical fiber sensor according to claim 4.

14. An optical shape sensing system, comprising:
an optical fiber sensor according to claim 4, and
an optical interrogation unit configured to interrogate the fiber cores of the first subset of fiber cores and the fiber cores of the second subset of fiber cores of the optical fiber sensor with light in a scan wavelength range and to measure reflection spectra received from the fiber cores of the first subset of fiber cores and the fiber cores of the second subset of fiber cores of the optical fiber sensor, and
an evaluation unit configured to reconstruct the shape of the fiber sensor using the reflection spectra.

15. The optical shape sensing system of claim 14, wherein the optical interrogation unit is configured to set the scan wavelength range such that a center wavelength of the scan wavelength range is decentered with respect to a first resonance wavelength of the fiber cores of the first subset, the resonance wavelength being in response to light introduced into the fiber cores of the first subset in an unstrained state of the fiber cores.

16. The optical shape sensing system of claim 14, wherein the optical interrogation unit is configured to set the scan wavelength range such that a center wavelength of the scan wavelength range is decentered with respect to a second resonance wavelength of the fiber cores of the second subset, the second resonance wavelength being in response to light introduced into the fiber cores of the second subset in an unstrained state of the fiber cores.

17. An optical shape sensing method, comprising:
providing an optical fiber sensor according to claim 4,
interrogating the fiber cores of the first subset of fiber cores and the fiber cores of the second subset of fiber cores with light,
measuring reflection spectra of light returning from the fiber cores of the first subset of fiber cores and the fiber cores of the second subset of fiber cores,
reconstructing the shape of the optical fiber sensor using the reflection spectra.

* * * * *